(12) United States Patent
Vescovi

(10) Patent No.: US 10,898,704 B2
(45) Date of Patent: Jan. 26, 2021

(54) TATTOO MACHINE HAVING AN ARM-MOUNTED POWER SUPPLY

(71) Applicant: Franco Vescovi, Lake Forest, CA (US)

(72) Inventor: Franco Vescovi, Lake Forest, CA (US)

(73) Assignee: Bishop Tattoo Supply, Inc., Lake Forest, CA (US)

( * ) Notice: Subject to any disclaimer, the term of this patent is extended or adjusted under 35 U.S.C. 154(b) by 1 day.

(21) Appl. No.: 15/675,885

(22) Filed: Aug. 14, 2017

(65) Prior Publication Data

US 2018/0043146 A1   Feb. 15, 2018

Related U.S. Application Data

(60) Provisional application No. 62/374,732, filed on Aug. 12, 2016.

(51) Int. Cl.
| | | |
|---|---|---|
| *A61M 37/00* | (2006.01) | |
| *A44C 5/00* | (2006.01) | |
| *H01R 13/66* | (2006.01) | |
| *H01R 13/62* | (2006.01) | |

(52) U.S. Cl.
CPC ....... *A61M 37/0076* (2013.01); *A44C 5/0007* (2013.01); *A61M 37/0084* (2013.01); *H01R 13/66* (2013.01); *H01R 13/6205* (2013.01)

(58) Field of Classification Search
CPC .......... A61M 37/0076; A61M 37/0084; A44C 5/0007; A44C 5/0023; A44C 5/003; H01R 13/66; H01R 13/6205; H01B 7/04; H01B 7/17; H01B 7/40
See application file for complete search history.

(56) References Cited

U.S. PATENT DOCUMENTS

| | | | |
|---|---|---|---|
| 180,857 A | 8/1876 | Edison | |
| 196,747 A | 11/1877 | Edison | |
| 464,801 A | 12/1891 | O'Reilly | |
| 6,550,356 B1 * | 4/2003 | Underwood | A61M 37/0084 30/362 |
| 7,442,042 B1 * | 10/2008 | Lewis | H01R 13/22 439/39 |
| 8,228,666 B2 * | 7/2012 | Rickard | A61M 37/0076 361/679.01 |
| 9,254,376 B2 * | 2/2016 | Colton | A61M 37/0076 |
| 9,582,035 B2 * | 2/2017 | Connor | G06F 1/163 |

(Continued)

OTHER PUBLICATIONS

Coil vs. Rotary Tattoo Machines| Painfulpleasures.Inc. Oct. 6, 2014.

(Continued)

*Primary Examiner* — David B. Thomas
(74) *Attorney, Agent, or Firm* — Burdick Patents, P.A.; Sean D. Burdick

(57) ABSTRACT

An arm-mounted motorized tattooing instrument includes a skin-perforating ink delivery wand configured for hand-held operation by a human operator, a wrist-or-forearm-mountable power supply, and a means for electrically coupling the skin-perforating ink delivery wand to the power supply. The instrument is configured to allow the human operator to operate the ink delivery wand without loss of power when rotating the ink delivery wand by hand about any of three orthogonal axes with the power supply mounted to a wrist or forearm of the same hand.

20 Claims, 3 Drawing Sheets

(56) References Cited

U.S. PATENT DOCUMENTS

| | | | |
|---|---|---|---|
| 9,836,900 B2* | 12/2017 | Jun | G07C 9/00119 |
| 9,980,539 B2* | 5/2018 | Webb | A44C 5/24 |
| 2005/0272401 A1* | 12/2005 | Zatezalo | G06F 1/163 |
| | | | 455/347 |
| 2008/0300615 A1* | 12/2008 | Colton | A61M 37/0076 |
| | | | 606/186 |
| 2009/0125049 A1* | 5/2009 | Copeland | A61M 37/0076 |
| | | | 606/186 |
| 2009/0236140 A1* | 9/2009 | Randall | H01R 13/03 |
| | | | 174/268 |
| 2010/0022285 A1* | 1/2010 | Randall | H01R 13/2421 |
| | | | 455/573 |
| 2010/0072827 A1* | 3/2010 | Norstrom | H01M 2/1022 |
| | | | 307/112 |
| 2016/0037874 A1* | 2/2016 | Webb | A44C 5/24 |
| | | | 224/267 |
| 2016/0099516 A1* | 4/2016 | Kim | H01R 13/6205 |
| | | | 361/752 |
| 2016/0120734 A1* | 5/2016 | Ishikawa | A45F 3/04 |
| | | | 601/151 |

OTHER PUBLICATIONS

Tattoo Artist Breaking News, Jay Brown: 28 Machine Builders Part I of IV| TAM Blog; Mar. 23, 2016.

* cited by examiner

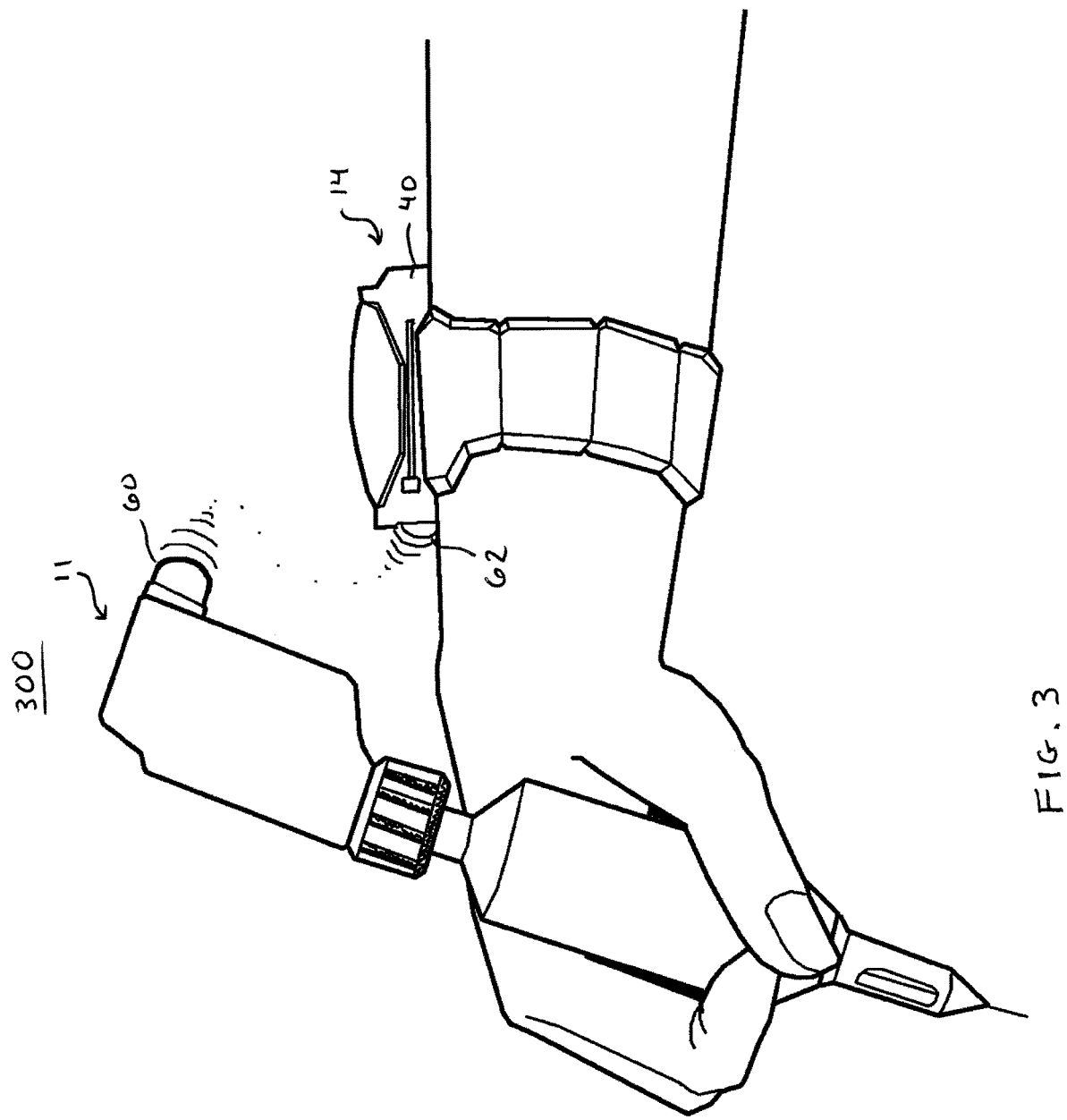

TATTOO MACHINE HAVING AN ARM-MOUNTED POWER SUPPLY

This application claims priority to U.S. Provisional Application 62/374,732, which was filed on Aug. 12, 2016, and which is fully incorporated herein by reference.

BACKGROUND OF THE INVENTION

Field of the Invention

The present invention relates generally to portable power supplies for hand-held power tools. More specifically, the invention relates to a body-mounted power supply for powering hand-held instruments, and most specifically the invention relates to an arm-mounted battery pack for powering a tattoo machine.

Description of Related Art

The first tattoo machine was derived from the design for an electric pen invented by Thomas Alva Edison in 1877, for which he was awarded U.S. Pat. No. 196,747. That machine used electromagnetic coils for driving a reciprocating pen and needle through paper to create a perforated pattern for autographic printing. In 1891, pioneering tattoo artist Samuel O'Reilly adapted Edison's device for tattooing by adding a tubular handle for delivering ink from an ink reservoir to the perforating needle. For this design O'Reilly was awarded U.S. Pat. No. 464,801.

From then til now, the basic components of a tattoo machine remain essentially unchanged. Tattoo machines all include some type of chassis adapted for hand-held operation that supports a motive force for actuating a linear motor. The motive force may be electromagnetic coils, a rotary electric motor, or a pneumatic motor. A pen coupled to the motive force and to a supply of tattooing ink is configured to inject the ink into the dermis layer of human skin upon each stroke of the motor. Most innovation for tattoo machines has addressed cosmetic desires or ergonomic concerns to give machines a different look and feel.

A persistent problem with tattoo machines that has been largely unaddressed is their unwieldy mass that hampers hand-held operation, particularly for tattoo artists who practice their craft for many hours each day. The weight of the coils or motor makes precision work more difficult, and limits how long an artist can work with the machine. Over time, tattoo artists who use these machines are at risk of suffering repetitive motion injuries such as carpal tunnel syndrome. Adding to the difficulty are the electric or pneumatic cords that supply power to the machine, as they tend to obstruct the artist's freedom of movement and can be generally annoying as he goes about his work. Wireless tattoo machines have been proposed to alleviate this problem, but these designs require batteries to be mounted on the machine, which adds even more mass to a machine that is already encumbered by the motor.

What is needed is a new configuration for a tattoo machine that provides adequate power while reducing mass and eliminating power supply cordage.

SUMMARY OF THE INVENTION

The present invention discloses an engineered design for an assembly consisting of a hand-held motorized tattooing instrument and an arm-mounted power supply for powering the hand-held motorized tattooing instrument. The assembly includes a skin-perforating ink delivery wand configured for hand-held operation by a human operator, a wrist-or-forearm-mountable power supply, and a flexible cable coupling the skin-perforating ink delivery wand to the wrist-or-forearm-mountable power supply. The assembly is configured to allow the human operator to operate the ink delivery wand without loss of power when rotating the ink delivery wand by hand about any of three orthogonal axes with the power supply mounted to a wrist or forearm of the same hand and electrically coupled to the tattooing instrument.

In another embodiment, the invention generally comprises a tattoo machine, having a motorized skin-perforating ink delivery means configured for hand-held operation by a human operator, an electric power source, a means for mounting the electric power source to the human operator separately from the ink delivery means, and a means for electrically coupling the electric power source to the ink delivery means.

The general configuration of a tattoo machine and power supply assembly according to the invention may be further configured in various ways, in more elaborate embodiments of the invention. For example, the tattoo machine may be configured for operation of the ink delivery means by a single hand of the human operator. The tattoo machine may be configured so that the electric power source comprises one or more batteries. The tattoo machine may be configured so that the electric power source outputs a pulse wave. The tattoo machine may be configured so that the mounting means comprises a wristband. The tattoo machine may be configured so that the wristband comprises a magnetic latch. The tattoo machine may be configured so that the mounting means comprises a display. The tattoo machine may be configured so that the display indicates battery voltage. The tattoo machine may be configured so that the mounting means further comprises a means for manually adjusting voltage output of the electric power source. The tattoo machine may be configured so that the mounting means further comprises a means for removal and installation of a battery by hand without the use of a tool. The tattoo machine may be configured so that the electrically coupling means comprises wireless power transmission. The tattoo machine may be configured so that the electrically coupling means comprises a flexible cable. The tattoo machine may be configured so that the flexible cable is configured to connect a coaxial output to an RCA input.

Another embodiment of the invention comprises an arm-mounted motorized tattooing instrument that includes a skin-perforating ink delivery wand configured for hand-held operation by a human operator, a wrist-mountable power supply, and a flexible cable coupling the skin-perforating ink delivery want to the arm-mountable power supply. The tattooing instrument may be further configured to allow the human operator to operate the ink delivery want without loss of power when rotating the ink delivery wand by hand about any of three orthogonal axes with the power supply mounted to a forearm of the same hand. The tattooing instrument may be further configured so that the arm-mountable power supply comprises one or more rechargeable batteries. The tattooing instrument may be further configured so that the arm-mountable power supply further comprises electronic circuitry outputting a pulse wave. The tattooing instrument may be further configured so that the arm-mountable power supply further comprises a display indicating output voltage. The tattooing instrument may be further configured so that the arm-mountable power supply comprises a means for manually adjusting the output voltage. The tattooing instrument may be configured so that the arm-mountable power supply further comprises a wristband having a magnetic latch.

BRIEF DESCRIPTION OF THE DRAWINGS

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. Component parts shown in the drawings are not necessarily to scale, and may be exaggerated to better illustrate the important features of the invention. Dimensions shown are exemplary only. In the drawings, like reference numerals may designate like parts throughout the different views, wherein:

FIG. 3 is a perspective view of another embodiment of the present invention, showing a hand-held motorized tattoo machine configured for wireless coupling to an arm-mounted power supply in the form of a wristband battery pack.

DETAILED DESCRIPTION OF THE INVENTION

The following disclosure presents exemplary embodiments for systems and methods that employ a wristband battery pack for use with tattoo machines according to the present invention. The instrument includes a skin-perforating ink delivery wand configured for hand-held operation by a human operator, a wrist-or-forearm-mountable power supply, and a means for electrically coupling the skin-perforating ink delivery wand to the wrist-or-forearm-mountable power supply. The instrument is configured to allow the human operator to operate the ink delivery wand without loss of power when rotating the ink delivery wand by hand about any of three orthogonal axes with the power supply mounted to a wrist or forearm of the same hand.

Figure 1:
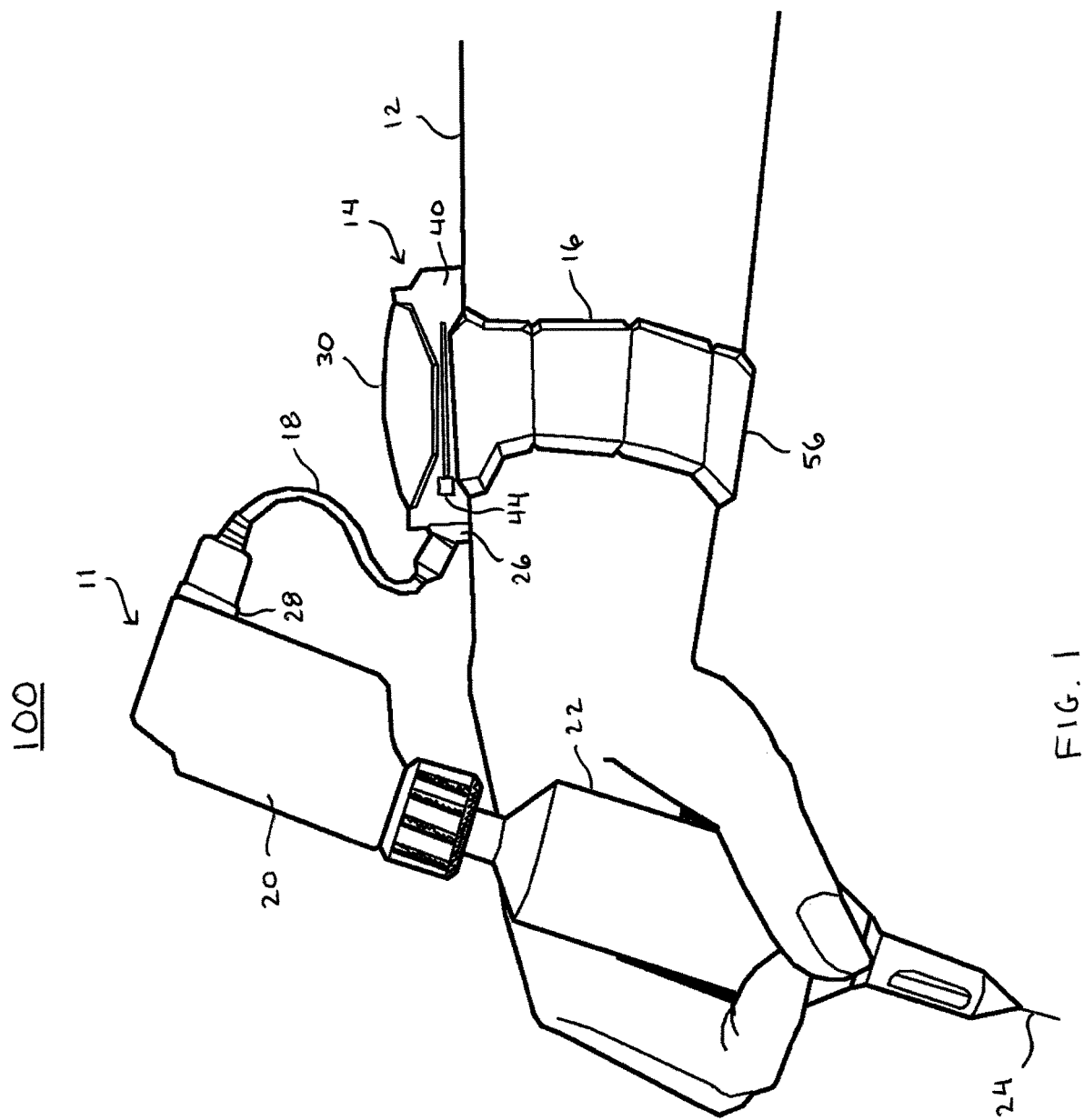
FIG. 1 is a perspective view of a tattoo machine having an arm-mounted power supply in the form of a wristband battery pack according to one embodiment of the present invention.

FIG. 1 shows a perspective view of an assembly for a tattoo machine 100 that utilizes a wristband battery back according to one embodiment of the present invention. The invention generally comprises a tattoo machine having a motorized skin-perforating ink delivery means 11 configured for hand-held operation by a human operator 12, an electric power source 14, a means 16 for mounting the electric power source 14 to the human operator 12 separately from the ink delivery means 11, and a means 18 for electrically coupling the electric power source 14 to the ink delivery means 11. In the embodiment shown, the motorized skin-perforating ink delivery means 11 includes an electric motor enclosed within a proximal enclosure 20, a linkage enclosed within a wand 22, and a distal tattooing needle 24 mechanically coupled to the electric motor by means of the linkage.

FIG. 1 illustrates one example of a means 18 for electrically coupling the electric power source 14 to the ink delivery means 11. In this example, the coupling means 18 is a flexible electric cable configured to connect a electrical output port 26 on the electric power source 14 to an RCA input 28 on the ink delivery means. The flexible electric cable may be a multi-conductor cable such as a coaxial cable, a two-conductor cable, a twisted pair cable, etc. In other embodiments, known connectors such as RCA, phono, coaxial, USB, ¼ inch, ⅛ inch, etc. may be used at one or both ends of the electrically coupling means. Flexibility of the cable is an advantageous feature of the invention, to provide sufficient slack to allow the operator freedom of movement of the hand bearing the ink delivery means during operation, without constricting that movement. In one embodiment the flexible cable or cord 18 will have a length of about 4 to 8 inches.

FIG. 1 also illustrates one exemplary arrangement of a mounting location and general configuration on the electric power source 14 for the electrical output port 26 that is configured for coupling to the electrically coupling means 18. The example output port 26 represents a ⅛ inch coaxial phono jack.

Figure 2:
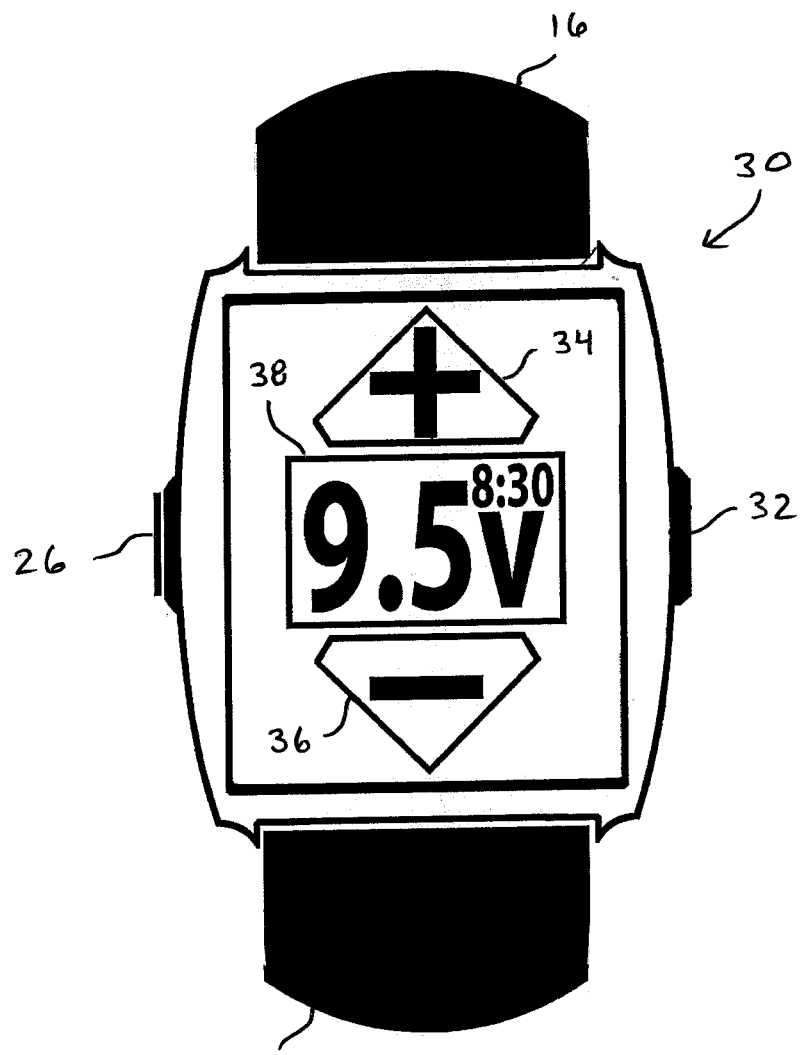
FIG. 2 is a magnified top view of one embodiment of a watch face of a wristband battery pack for an arm-mounted power supply according to the present invention.

Also illustrated in FIG. 1 is one exemplary embodiment of a watch face or digital display 30 located on top of the wrist-mounted electric power source 14. FIG. 2 shows a magnified top view of another embodiment of a watch face 30 for use on a wristband battery pack for an arm-mounted power supply according to the present invention. The exemplary embodiment depicted in the magnified view shows various user interface displays or controls. The electrical port 26 (phono jack or RCA female connector) is shown on the left side of the watch face 30. An on/off button 32 may be provided on an opposite side of the watch face 30, as shown. Hand-operated voltage adjustment buttons 34 (+) and 36 (−) may be provided on the top of the watch face (as shown) or in another convenient location to allow the operator to raise (+) or lower (−) the output voltage of the power source 14. A digital display 38, such as an OLED display, may be provided on the watch face 30 to indicate the actual output voltage. Other features, such as the time of day, battery charge remaining, operating time remaining, operating time elapsed, etc., may also be displayed on the watch face 30.

Referring again to FIG. 1, power source 14 includes a body or chassis 40 for containing a source of electric power according to the invention. In this illustration, the body 40 of the power source 14 resembles a generally rectangular watch casing. The body 40 may be preferably formed from a strong, relatively lightweight noncorrosive material such as metal (e.g. stainless steel, plated steel, or aluminum) or from a molded high-quality polymer. The body 40 may be configured to support a transparent cover for the watch face, and must provide an enclosed volume for housing one or more batteries, integrated circuits, small-scale electronics, and associated conductors and insulators. In one embodiment, the body 40 defines a slot 42 that is sized for accepting a battery. In one embodiment, the body 40 defines a hollow rectangular base having an area of about 1.5×0.5 inches for accommodating a battery. The slot 40 cooperates with a locking mechanism, such as a spring-loaded latch 44, that allows a battery 46, such as a lithium or other type battery having a generally rectangular or circular form, or a rectangular form with rounded edges, to be inserted by hand through the slot 40 and into the hollow rectangular base of body 40 until the locking mechanism 44 releasably engages the battery 46 into operable electrical connection with the output port 26.

Figure 4:
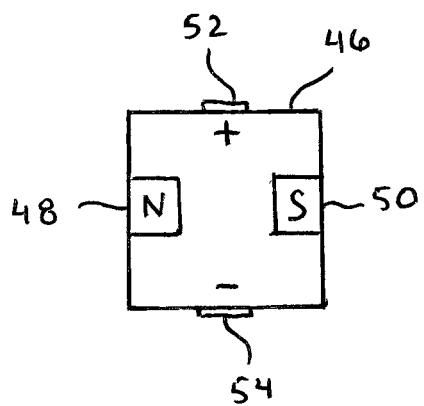
FIG. 4 is a top view of one embodiment of a battery assembly for use within an arm-mounted power supply according to the present invention.

FIG. 4 illustrates one embodiment of a battery or battery assembly 46 for use within a tattoo machine according to the present invention. The battery 46 is configured with a plurality of magnetic surfaces 48 and 50, which correspond respectively to the north and south poles of a magnet. The poles 48 and 50 cooperate with complementary magnetic surfaces mounted within the slot, so that the battery, responsive to magnetic forces, will automatically align for proper electrical connection of its positive 52 and negative 54 terminals when inserted into the power supply body 40. A battery release button, such as spring-loaded latch 44, allows an operator 12 to disengage the battery 46 from the power supply body 40 by depressing the latch, e.g., with thumb or forefinger.

The battery or batteries 46 enclosed within the body 40 are sized to provide sufficient electrical power to operate the ink delivery means 11 for a desired time period, in response to an operator 12 switching the on/off button 32 to the on position. When battery power runs out, the releasably engageable locking mechanism 44 allows the operator to quickly and easily replace the spent battery with another battery that is fully charged. In one embodiment, the electronics housed within the body 40 include circuitry for converting DC output voltage to pulse waves for optimizing battery life. In one embodiment, the battery or batteries 46 are selected to provide an output in the range of 3 to 20 VDC, continuous or pulsed, to power an electric motor mounted within the ink delivery means 11. In another embodiment, the battery or batteries 46 are rated for an output of 9 to 10 VDC, continuous or pulsed. In one embodiment, the battery or batteries 46 may comprise a Panasonic cell type NCA793540.

Referring again to FIG. 1, shown therein is one exemplary embodiment of a wristband or watch band 16 that functions as a means for mounting the electric power source 14 to the wrist or forearm of a human operator 12. The wristband 16 may be segmented, as shown, or consist of two or more interlocking straps.

Also depicted in FIG. 1 is one exemplary embodiment of an skin-perforating ink delivery means 11 of a tattoo machine according to the invention. The particular configuration shown is illustrative only, as the wrist-mounted or forearm-mounted power supply is designed for operation with many different types of electrically powered ink delivery means or tattooing wands. Power is supplied to these tattooing devices via the coupling means 18 that may connect to an electrical port such as electrical port 28 that is mounted to the enclosure 20. The electrical port 28 couples DC power to the terminals of a motor housed within the ink delivery means 11. Generally, the DC motor ratings are commensurate with those commonly found in today's remote controlled toy cars.

FIG. 1 also illustrates one exemplary embodiment of a magnetic closure for the watch band 16. The magnetic closure includes complimentary magnetic surfaces on adjacent segments 56 or straps 56 of the watch band 16, each segment or strap 56 configured to allow an operator 12 to quickly and easily secure the watch band 16 around his wrist when opposing ends of the straps or segments 56 are brought into close proximity and allowed to engage by magnetic force. This allows the operator 12 to connect the watch band around his wrist or forearm using one free hand.

FIG. 3 illustrates another embodiment of the present invention. In this embodiment, a hand-held motorized tattoo machine 300 is configured for wireless coupling for power transfer between a skin-perforating ink delivery wand 11 and an arm-mounted power supply 14 in the form of a wristband battery pack. Otherwise, the general configuration and operation of the tattoo machine 300 is similar to that of tattoo machine 100. Tattoo machine 300 is further characterized by its wireless configuration that allows for either radiative or inductive coupling between the wand 11 and the power supply 14. The wireless coupling means is represented by wireless coupling nodes 60 and 62. Because the proximity of these nodes is about 3 to 5 inches, coupling therebetween may be achieved by either magnetic induction or electromagnetic radiation. In one embodiment, the nodes 60 and 62 represent encapsulated conductors or coils configured for intercoupling by means of magnetic induction. In another embodiment, nodes 60 and 62 represent antennae configured for intercoupling by electromagnetic transception. In either of these embodiments, when on/off button 32 is switched on, electrical circuitry enclosed within the body 40 causes electrical current to flow from the battery or batteries 46 stored within power source 14 to node 62 to transmit electrical energy wirelessly from node 62 to be received by node 60.

The general configuration of a tattoo machine described herein may be further configured in various ways, in more elaborate embodiments of the invention. For example, the tattoo machine may be configured for operation of the ink delivery means by a single hand of the human operator. The tattoo machine may be configured so that the electric power source comprises one or more batteries. The tattoo machine may be configured so that the electric power source outputs a pulse wave. The tattoo machine may be configured so that the mounting means comprises a wristband. The tattoo machine may be configured so that the wristband comprises a magnetic latch. The tattoo machine may be configured so that the mounting means comprises a display. The tattoo machine may be configured so that the display indicates battery voltage. The tattoo machine may be configured so that the mounting means further comprises a means for manually adjusting voltage output of the electric power source. The tattoo machine may be configured so that the mounting means further comprises a means for removal and installation of a battery by hand without the use of a tool. The tattoo machine may be configured so that the electrically coupling means comprises wireless power transmission. The tattoo machine may be configured so that the electrically coupling means comprises a flexible cable. The tattoo machine may be configured so that the flexible cable is configured to connect a coaxial output to an RCA input.

Another embodiment of the invention comprises an arm-mounted motorized tattooing instrument that includes a skin-perforating ink delivery wand configured for hand-held operation by a human operator, an arm-mountable power supply, and a flexible cable coupling the skin-perforating ink delivery want to the arm-mountable power supply. The tattooing instrument may be further configured to allow the human operator to operate the ink delivery want without loss of power when rotating the ink delivery wand by hand about any of three orthogonal axes with the power supply mounted to a wrist or forearm of the same hand. The tattooing instrument may be further configured so that the arm-mountable power supply comprises one or more rechargeable batteries. The tattooing instrument may be further configured so that the arm-mountable power supply further comprises electronic circuitry outputting a pulse wave. The tattooing instrument may be further configured so that the arm-mountable power supply further comprises a display indicating output voltage. The tattooing instrument may be further configured so that the arm-mountable power supply comprises a means for manually adjusting the output voltage. The tattooing instrument may be configured so that the arm-mountable power supply further comprises a wristband having a magnetic latch.

A wrist-or-forearm-mounted power source according to the invention allows a tattoo artist more freedom of movement when tattooing because transferring the weight of the batteries from the ink-delivery means to the wrist or forearm places less burden on the artist's hand. It also allows the artist more freedom of movement by allowing the artist to stand up and move around his client without having his movement restricted by an electrical cable that tethers the tattooing instrument to an electrical outlet, or that otherwise obstructs the free movement of the artist's hands or legs.

The invention further contemplates a specialized battery charging station that is able to recharge three or more batteries at a time, so that the artist can always have at least two batteries charging while using one in the power source of the tattooing machine. Spent batteries can therefore be quickly and easily replaced with fully charged batteries to allow the artist to continue his work with minimal interruption.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A tattoo machine, comprising:
   a motorized skin-perforating ink delivery means configured for hand-held operation by a human operator;
   an electric power source sized to provide power to an electric motor housed within the ink delivery means;
   means for mounting the electric power source to a wrist of the human operator separately from the ink delivery means; and
   means for wirelessly transmitting the power to the electric motor when the electric power source is mounted to the wrist of a hand with which the operator grasps the ink delivery means.

2. The tattoo machine of claim 1 wherein the ink delivery means is configured for operation by a single hand of the human operator.

3. The tattoo machine of claim 1 wherein the electric power source comprises one or more batteries.

4. The tattoo machine of claim 1 wherein the electric power source outputs a pulse wave.

5. The tattoo machine of claim 1 wherein the mounting means comprises a wristband.

6. The tattoo machine of claim 5 wherein the wristband comprises a magnetic latch.

7. The tattooing instrument of claim 5 wherein the arm-mountable power supply further comprises a wristband having a magnetic latch.

8. The tattoo machine of claim 1 wherein the mounting means comprises a display.

9. The tattoo machine of claim 8 wherein the display indicates battery voltage.

10. The tattoo machine of claim 1 wherein the mounting means further comprises a means for manually adjusting voltage output of the electric power source.

11. The tattoo machine of claim 1 wherein the mounting means further comprises a means for removal and installation of a battery by hand without the use of a tool.

12. The tattoo machine of claim 1 wherein the electrically coupling means comprises a flexible cable.

13. The tattoo machine of claim 12 wherein the flexible cable is configured to connect a coaxial output to an RCA input.

14. The tattooing instrument of claim 1 configured to allow the human operator to operate the ink delivery want without loss of power when rotating the ink delivery wand by hand about any of three orthogonal axes with the power supply mounted to an arm of the same hand.

15. The tattooing instrument of claim 14 wherein the arm-mountable power supply comprises one or more rechargeable batteries.

16. The tattooing instrument of claim 15 wherein the arm-mountable power supply further comprises electronic circuitry outputting a pulse wave.

17. The tattooing instrument of claim 15 wherein the arm-mountable power supply further comprises a display indicating output voltage.

18. The tattooing instrument of claim 17 wherein the arm-mountable power supply further comprises a means for manually adjusting the output voltage.

19. The tattoo machine of claim 1 wherein the electric power source comprises a battery case configured with magnetic alignment poles and a battery having a magnetic case configured for magnetic alignment with the magnetic alignment poles of the battery case, so that placement of the battery within the battery case by the operator causes automatic electrical connection of the battery to the battery case.

20. An arm-mounted motorized tattooing instrument, comprising:
   a skin-perforating ink delivery wand configured for hand-held operation by a human operator;
   an arm-mountable power supply; and
   a flexible cable coupling the skin-perforating ink delivery want to the arm-mountable power supply;
   wherein the arm-mountable power supply comprises a battery case configured with magnetic alignment poles and a battery having a magnetic case configured for magnetic alignment with the magnetic alignment poles of the battery case, so that placement of the battery within the battery case by the operator causes automatic electrical connection of the battery to the battery case.

* * * * *